United States Patent [19]

Punja

[11] Patent Number: 4,551,546
[45] Date of Patent: Nov. 5, 1985

[54] HALOGENATED ESTERS

[75] Inventor: Nazim Punja, Crowthorne, England

[73] Assignee: Imperial Chemical Industries PLC, London, England

[21] Appl. No.: 551,697

[22] Filed: Nov. 14, 1983

Related U.S. Application Data

[60] Continuation of Ser. No. 339,733, Jan. 15, 1982, , which is a division of Ser. No. 211,943, Dec. 1, 1980, Pat. No. 4,405,640.

[30] Foreign Application Priority Data

Dec. 21, 1979 [GB] United Kingdom ............... 7944151
Nov. 20, 1980 [GB] United Kingdom ............... 8037257

[51] Int. Cl.$^4$ .................. A01N 53/00; C07C 69/74
[52] U.S. Cl. ................................................. 560/124
[58] Field of Search ................... 560/124; 514/531

[56] References Cited

U.S. PATENT DOCUMENTS

| | | |
|---|---|---|
| 3,338,979 | 8/1967 | Gilbert et al. ............... 570/127 |
| 3,385,901 | 5/1968 | Tamborski et al. ............ 568/812 |
| 3,459,794 | 8/1969 | Tamborski .................. 562/493 |
| 3,544,535 | 12/1970 | Gilbert et al. ............... 568/812 |
| 3,714,276 | 1/1973 | Pierce et al. ................ 568/812 |
| 4,075,238 | 2/1978 | Mark et al. ................. 568/812 |

FOREIGN PATENT DOCUMENTS

| | | |
|---|---|---|
| 2658074 | 7/1978 | Fed. Rep. of Germany ...... 562/493 |
| 977961 | 12/1964 | United Kingdom ............ 562/493 |

*Primary Examiner*—Paul J. Killos
*Attorney, Agent, or Firm*—Cushman, Darby & Cushman

[57] ABSTRACT

This invention relates to novel cyclopropane derivatives useful as insecticides, to processes for their preparation, to compositions comprising them and to methods of combatting insect and similar invertebrate pests using them.

4 Claims, No Drawings

HALOGENATED ESTERS

This is a continuation of application Ser. No. 339,733, filed Jan. 15, 1982, which is a division of Ser. No. 211,943, filed Dec. 1, 1980, now U.S. Pat. No. 4,405,640.

Accordingly this invention provides compounds of formula:

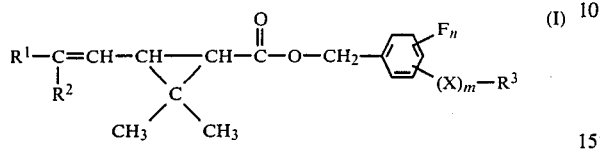
(I)

wherein $R^1$ and $R^2$ are each selected from methyl, halomethyl, and halo; X is oxygen, sulphur, sulphonyl or a group $NR^4$ where $R^4$ represents hydrogen, lower alkyl or lower carboxylic acyl; $R^3$ is lower alkyl, lower alkenyl or benzyl; m has the value zero or one, and n has a value from one to four.

The term "lower" is used herein in relation to "alkyl", "alkenyl" and "carboxylic acyl" groups to indicate such groups containing up to six carbon atoms, although such groups containing up to four carbon atoms are generally preferred.

In a preferred aspect the invention provides compounds of formula:

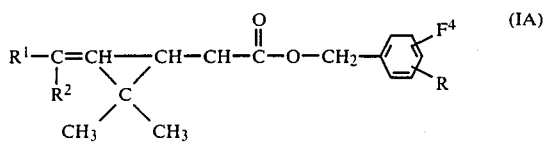
(IA)

wherein $R^1$ and $R^2$ are both chloro, or one of $R^1$ and $R^2$ is chloro and the other is trifluoromethyl, and R is methyl, ethyl, allyl, methoxy, ethoxy, allyloxy, ethylthio, ethylsulphonyl, dimethylamino, ethylamino, acetamido or N-methylacetamido. R is preferably in the 2- or 4-position with respect to the cyclopropane ester group.

Particular compounds according to the invention as defined by formula IA above include those set out in Table I herein in which the meanings for $R^1$, $R^2$ and R are given for each compound.

TABLE I

| Compound No. | $R^1$ | $R^2$ | R |
|---|---|---|---|
| 1 | $CF_3$ | Cl | 4-$CH_3$ |
| 2 | $CF_3$ | Cl | 4-$SC_2H_5$ |
| 3 | Cl | Cl | 4-$CH_3$ |
| 4 | $CF_3$ | Cl | 4-$SO_2C_2H_5$ |
| 5 | $CF_3$ | Cl | 4-$OCH_3$ |
| 6 | $CF_3$ | Cl | 2-$CH_3$ |
| 7 | $CF_3$ | Cl | 4-$OC_2H_5$ |
| 8 | Cl | Cl | 4-$OC_2H_5$ |
| 9 | Cl | Cl | 4-$C_2H_5$ |
| 10 | $CF_3$ | Cl | 4-$C_2H_5$ |
| 11 | Cl | Cl | 4-$OCH_3$ |
| 12 | Cl | Cl | 4-$CH_2CH=CH_2$ |
| 13 | $CF_3$ | Cl | 4-$CH_2CH=CH_2$ |
| 14 | Cl | Cl | 4-$OCH_2CH=CH_2$ |
| 15 | $CF_3$ | Cl | 4-$n$-$C_4H_9$ |
| 16 | $CF_3$ | Cl | 4-$OCH_2CH=CH_2$ |
| 17 | $CF_3$ | Cl | 3-$CH_3$ |
| 18 | Cl | Cl | 3-$CH_3$ |
| 19 | $CF_3$ | Cl | 4-$n$-$C_3H_7$ |
| 20 | $CF_3$ | Cl | 4-$CH_2CH=C(CH_3)_2$ |
| 21 | $CF_3$ | Cl | 4-$CH_2CH=CHCH_3$ |

TABLE I-continued

| Compound No. | $R^1$ | $R^2$ | R |
|---|---|---|---|
| 22 | $CF_3$ | Cl | 4-$CH_2C_6H_5$ |
| 23 | $CF_3$ | F | 4-$NHCOCH_3$ |
| 24 | $CF_3$ | F | 4-$N(CH_3)COCH_3$ |
| 25 | $CF_3$ | F | 4-$N(C_2H_5)_3$ |
| 26 | Br | Br | 4-$OCH_3$ |
| 27 | $CH_3$ | $CH_3$ | 4-$OCH_3$ |
| 28 | $CH_3$ | $CH_3$ | 4-$CH_2CH=CH_2$ |

Further compounds according to the invention include those of formula I above in which n is an integer of less than 4. Examples of such compounds are set out in Table II below.

TABLE II

| Compound No. | $R^1$ | $R^2$ | aryl group |
|---|---|---|---|
| 29 | $CF_3$ | Cl | 2,6-difluoro-4-($CH_2CH=CH_2$)-phenyl |
| 30 | $CF_3$ | Cl | 2,3-difluoro-4-($CH_2CH=CH_2$)-phenyl |

It will be appreciated by those skilled in the art that the compounds represented by formula I are capable of existing in various geometrical and stereoisomeric forms. Thus there may be cis and trans isomers arising from the substitution pattern of the cyclopropane ring, and E- and Z-isomers arising from the substituted vinyl group when $R^1$ is not identical with $R^2$. In addition two of the three carbon atoms of the cyclopropane are capable of existing in either R- or S-configurations since they are asymmetrically substituted. Within the group of compounds represented by Formula I the cis isomers usually have better insecticidal properties than the trans isomers or the mixture of cis and trans isomers; the (+)-cis isomers being particularly preferred.

A particularly useful single isomer of a compound according to the invention is the 4-methyltetrafluorobenzyl ester of (+)-cis-3-(Z-2-chloro-3,3,3-trichloroprop-1-en-yl)-2,2-dimethylcyclopropane carboxylic acid, which is believed to have the (1R,3R) configuration in the cyclopropane ring.

The compounds of the invention according to Formula I are esters and may be prepared by conventional esterification processes, of which the following are examples.

(a) An acid of formula:

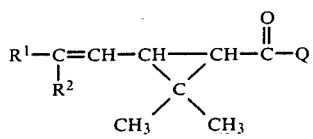

where Q represents the hydroxy group and $R^1$ and $R^2$ have any of the meanings given hereinabove, may be reacted directly with an alcohol of formula:

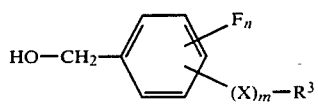

where X, $R^3$, n and m have any of the meanings given hereinabove, the reaction preferably taking place in the presence of an acid catalyst, for example, dry hydrogen chloride.

(b) An acid halide of formula II where Q represents a halogen atom, preferably a chlorine atom, and $R^1$ and $R^2$ have any of the meanings given hereinabove, may be reacted with an alcohol of formula III, the reaction preferably taking place in the presence or a base, for example, pyridine, alkali metal hydroxide or carbonate, or alkali metal alkoxide.

(c) An acid of formula II where Q represents the hydroxy group or, preferably, an alkali metal salt thereof, may be reacted with halide of formula:

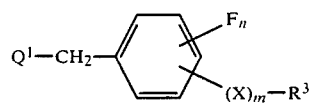

where $Q^1$ represents a halogen atom, preferably the chlorine atom, X, $R^3$, m and n have any of the meanings given hereinabove, or with the quaternary ammonium salts derived from such halides with tertiary amines, for example pyridine, or trialkyl amines such as triethylamine.

(d) A lower alkyl ester of formula (II) where Q represents a lower alkoxy group containing up to six carbon atoms, preferably the methoxy or ethoxy group, and $R^1$ and $R^2$ have any of the meanings given hereinabove, is heated with an alcohol of formula III to effect a transesterification reaction. Preferably the process is performed in the presence of a suitable catalyst, for example, an alkali metal alkoxide, such as sodium methoxide, or an alkylated titanium derivative, such as tetramethyl titanate.

All of these conventional processes for the preparation of esters may be carried out using solvents and diluents for the various reactants where appropriate, and may be accelerated or lead to higher yields of product when performed at elevated temperatures or in the presence of appropriate catalyst, for example phase-transfer catalysts.

The preparation of individual isomers may be carried out in the same manner but commencing from the corresponding individual isomers of compounds of formula II. These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid.

The optically pure isomeric form of the acid (or its equivalent acid chloride or ester) may then be reacted with the appropriate alcohol to produce a compound of formula I in the form of an individually pure isomer thereof.

The preparation of the compounds of formula II wherein Q is hydroxy, alkoxy or halo, and $R^1$ and $R^2$ are as defined hereinabove, useful as intermediates in the preparation of the compounds of the invention, is fully described in British Patent Specification No. 2,000,764 and in Belgian Pat. No. 863151, or British Patent Specification No. 1,413,491.

The compounds of formulae III and IV are believed not to have been described before. In a further aspect therefore the invention provides compounds of formulae III and IV wherein X, $R^3$, m and n have any of the meanings given for the corresponding compounds of formula I, and where $Q^1$ (in formula IV) is chloro or bromo. Preferred compounds of formulae III and IV are those corresponding to the compounds set out in Table I.

The compounds of formula III may be prepared by different processes depending upon the nature of the substituents in the benzene ring. Thus for alkyl- or alkenyl- substituted compounds of formula III where $R^3$ is alkyl and m is zero the appropriately substituted alkyl- or alkenyl- fluorobenzene may be carboxylated (for example by the use of an organometallic reagent such as alkyl lithium, followed by decomposition of the reaction product with carbon dioxide) and subsequent reduction to the alcohol, using an appropriate reducing reagent, for example, lithium aluminium hydride.

The alkyl- or alkenyl- substituted fluorobenzenes used as starting materials in this sequence may be prepared by the alkylation of the appropriate fluorobenzenes using organometallic reagents such as alkyl lithium, and decomposing the reaction products with alkyl or alkenyl halides.

Alternatively the fluorobenzenes may be carboxylated first, and the resultant fluorobenzoic acids reduced to the benzyl alcohol which is then alkylated or alkenylated in a protected form (for example as the tetrahydropyranyl ether) using alkyllithium followed by reaction with an alkyl or alkenyl halide.

All of these processes are illustrated in the following scheme.

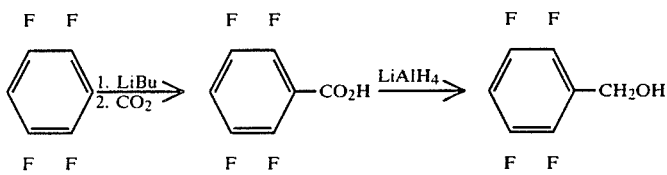

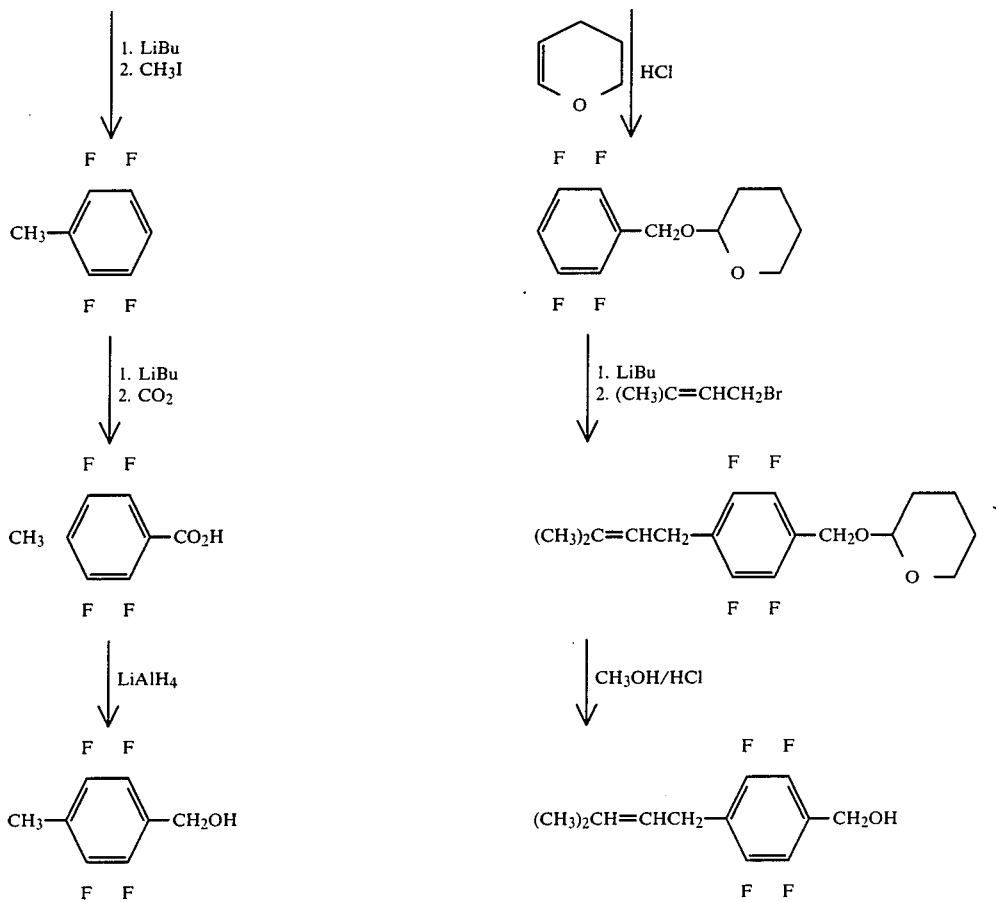
The compounds of formula III wherein X is sulphur or oxygen, may be prepared by displacement of halogen, e.g. fluorine, from an appropriately substituted fluoro- benzyl alcohol, or the tetrahydropyranyl ether thereof. The following scheme illustrates the reactions used to prepare a number of compounds of formula III.
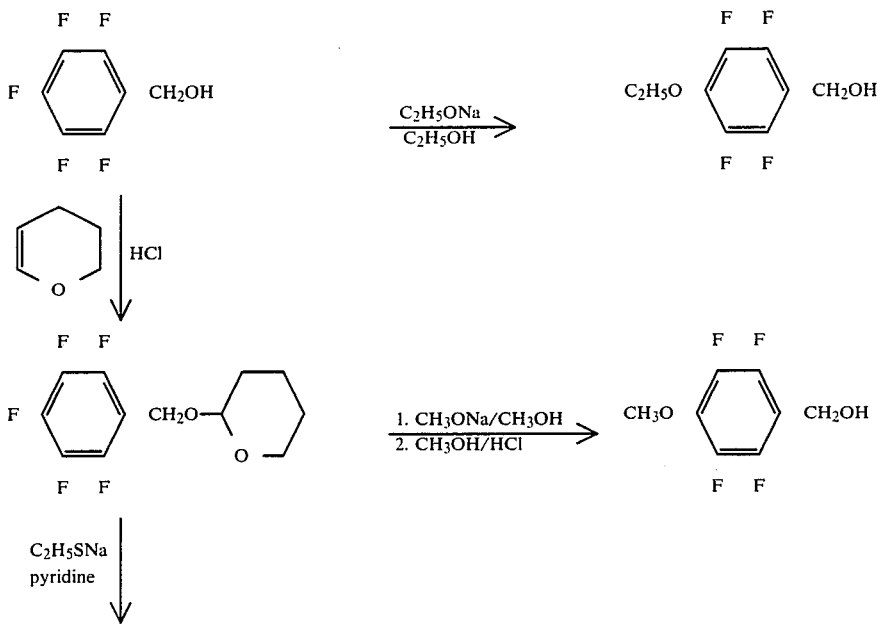

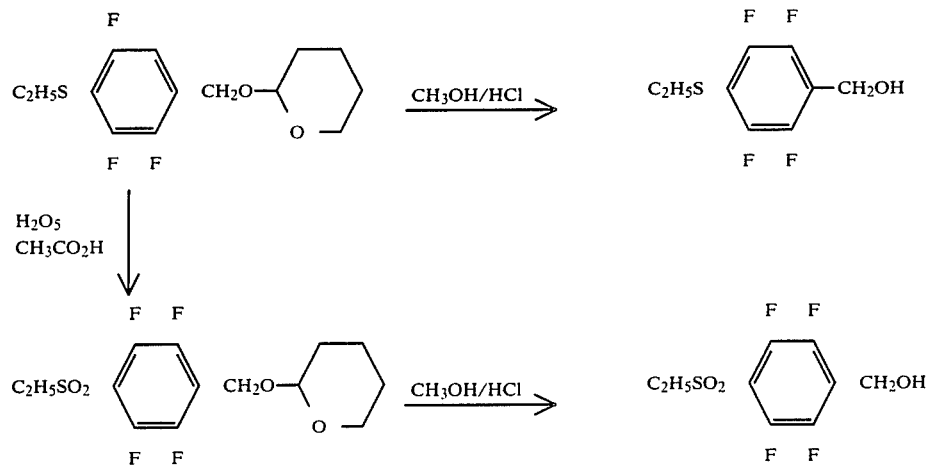
Similarly the compounds of formula III where X represents a group of formula NR⁴ (where R⁴ is as defined hereinbefore) may also be obtained from the corresponding fluorobenzyl alcohol. The following scheme illustrates the reactions involved in preparing some of these compounds.
Compounds of formula IV may be prepared by contacting a compound of formula
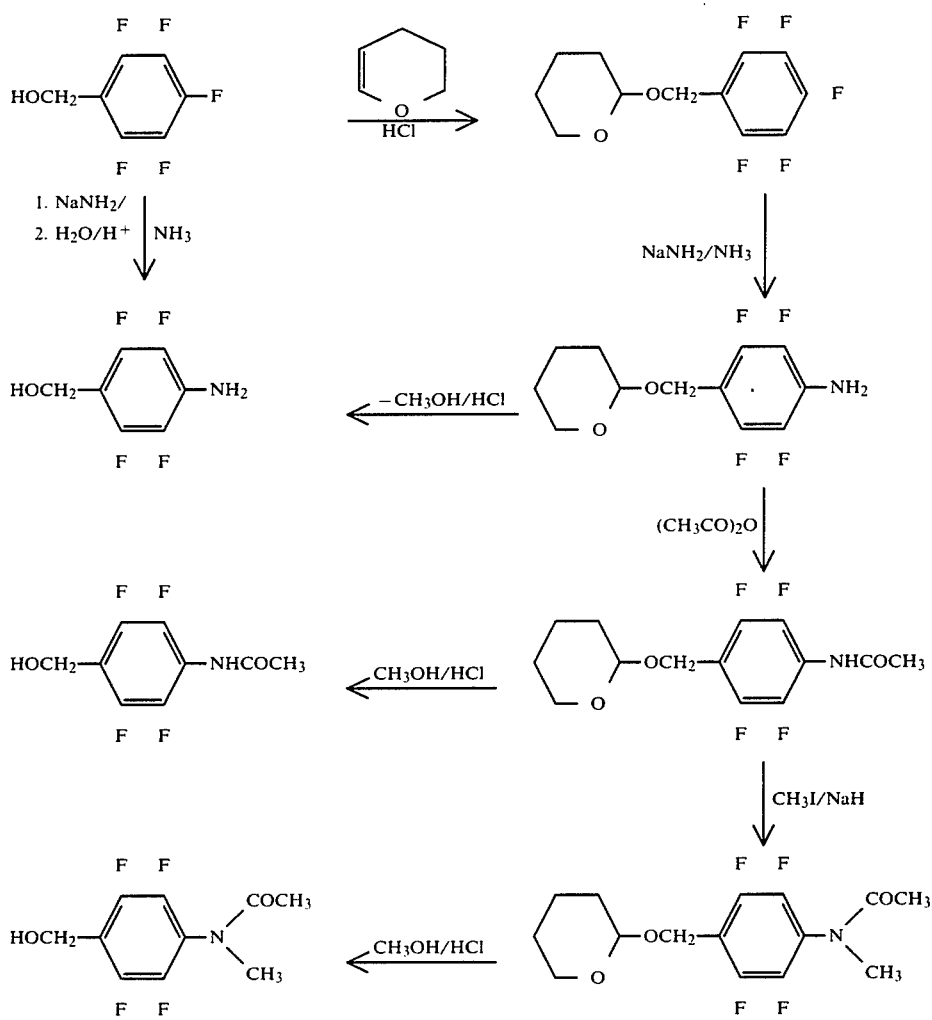

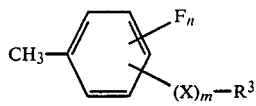

with a source of positive halogen, such as an N-chloro- or N-bromoimide, for example, N-chlorosuccinimide and N-bromosuccinimide.

When the processes for preparing the compounds of Formula I are performed using intermediates which are themselves mixtures of isomers the products obtained will also be mixtures of isomers. Thus, the product would be a mixture of (±)-cis and (±)-trans isomers (perhaps with one form predominating) if the intermediate acid or acid derivative was used in the form of a mixture of (±)-cis and (±)-trans isomers. If a single isomer, of the acid, e.g. the (+)-cis isomer with Z-configuration in the 2-chloro-3,3,3-trifluoropropenyl group, was used, the product would also be the single isomer of that stereochemical configuration, or a pair of isomers if there is an asymmetric carbon atom in the alcohol moiety.

In order to avoid confusion the products obtained by the processes described in the Examples herein are referred to as Products A to Z, each product being defined in terms of isomeric composition with reference to the compounds of Tables I and III as follows:

Product A: 4-methyltetrafluorobenzyl 3-(2-chloro-3,3,3-trifluoroprop-1-en-1-yl)-2,2-dimethylcyclopropane carboxylate (compound no. 1, Table I) consisting of 50% w/w of the (±)-cis isomer and 50% w/w of the (±)-trans isomer Product B: 4-ethylthiotetrafluorobenzyl 3-(2-chloro-3,3,3-trifluoroprop-1-en-1-yl)-2,2-dimethylcyclopropane carboxylate (compound no.2, Table I) consisting of 50% w/w of the (±)-cis isomer and 50% w/w of the (±)-trans isomer Product C: 4-methyltetrafluorobenzyl 3-(2,2-dichlorovinyl)-2,2-dimethylcyclopropane carboxylate (compound No.3, Table I) consisting of 50% w/w of the (±)-cis isomer and 50% w/w of the (±)-trans isomer Product D: 4-ethanesulphonyltetrafluorobenzyl 3-(2-chloro-3,3,3-trifluoroprop-1-en-1-yl)-2,2-dimethylcyclopropane carboxylate (compound no. 4, Table I) consisting of 50% w/w of the (±)-cis isomer and 50% w/w of the (±)-trans isomer Product E: 4-methoxytetrafluorobenzyl 3-(2-chloro-3,3,3-trifluoroprop-1-en-1-yl)-2,2-dimethylcyclopropane carboxylate (compound no. 5, Table I) consisting of 50% w/w of the (±)-cis isomer and 50% w/w of the (±)-trans isomer.

Product F: 2-methyltetrafluorobenzyl 3-(2-chloro-3,3,3-trifluoroprop-1-en-1-yl)-2,2-dimethylcyclopropane carboxylate (compound no. 6, Table I) consisting of 50% w/w of the (±)-cis isomer and 50% w/w of the (±)-trans isomer.

Product G: 4-ethoxytetrafluorobenzyl 3-(2-chloro-3,3,3-trifluoroprop-1-en-1-yl)-2,2-dimethylcyclopropane carboxylate (compound no. 7, Table I) consisting of 50% w/w of the (±)-cis isomer and 50% w/w of the (±)-trans isomer.

Product H: 4-ethoxytetrafluorobenzyl 3-(2,2-dichlorovinyl)-2,2-dimethylcyclopropane carboxylate (compound no. 8, Table I) consisting of 50% w/w of the (±)-cis isomer and 50% w/w of the (±)-trans isomer.

Product J: 4-methyltetrafluorobenzyl (±)-cis-3-(2,2-dichlorovinyl)-2,2-dimethylcyclopropane carboxylate (compound no. 3, Table I) in its (±)-cis isomer form.

Product K: 4- methyltetrafluorobenzyl 3-(2-chloro-3,3,3-trifluoroprop-1-en-1-yl)-2,2,-dimethylcyclopropane carboxylate (compound no. 1, Table I) in its (±)-cis isomeric form.

Product L: 4-methyltetrafluorobenzyl 3-(2-chloro-3,3,3-trifluoroprop-1-en-1-yl)-2,2-dimethylcyclopropane carboxylate (compound no. 10, Table I) in its (±)-cis isomeric form.

Product M: 4-methoxytetrafluorobenzyl 3-(2,2-dichlorovinyl)2,2-dimethylcyclopropane carboxylate (compound no. 11, Table I) in its (±)-cis isomeric form.

Product N: 4-n-butyltetrafluorobenzyl 3-(2-chloro-3,3,3-trifluoroprop-1-en-1-yl)-2,2-dimethylcyclopropane carboxylate (compound no. 15, Table I) in its (±)-cis isomeric form.

Product O: 4-alkoxytetrafluorobenzyl 3-(2-chloro-3,3,3-trifluoroprop-1-en-1-yl)-2,2-dimethylcyclopropane carboxylate (compound no. 16, Table I) in its (±)-cis isomeric form.

Product P: 4-methoxytetrafluorobenzyl 3-(2-chloro-3,3,3-trifluoroprop-1-en-1yl)-2,2-dimethylcyclopropane carboxylate (compound no. 5, Table I) in its (±)-cis isomeric form.

Product Q: 3-methyltetrafluorobenzyl 3-methyltetrafluorobenzyl 3-(2-chloro-3,3,3-trifluoroprop-1-en-1-yl)-2,2-dimethylcyclopropane carboxylate (compound no. 17, Table I) in its (±)-cis isomeric form.

Product R: 3-(2,2-dichlorovinyl)-2,2-dimethylcyclopropane carboxylate (compound no. 18, Table I) consisting of 50% w/w of the (±)-cis isomer and 50% w/w of the (±)-trans isomer.

Product S: 4-allytetrafluorobenzyl 3-(2-chloro-3,3,3-trifluoroprop-1-en-1yl)-2,2-dimethylcyclopropane carboxylate (compound no. 13, Table I) in its (±) cis isomeric form.

Product T: 4n-propyltetrafluorobenzyl 3-(2-chloro-3,3,3-trifluoroprop-1-en-1-yl)-2,2-dimethylcyclopropane carboxylate (compound no. 19, Table I) in its (±)-cis isomeric form.

Product U: 4-allyltetrafluorobenzyl 3-(2,2-dichlorovinyl)-2,2-dimethylcyclopropane carboxylate (compound no. 12, Table I) consisting of 50% w/w of the (±)-cis isomer and 50% w/w of the (±)-trans isomer.

Product V: 4-(3-methylbut-2-en-1-yl)tetrafluorobenzyl 3-(2-chloro-3,3,3-trifluoroprop-1-en-1-yl)-2,2-dimethylcyclopropane carboxylate (compouond no. 20, Table I) in its (±)-cis isomeric form.

Product W: 4-(but-2-en-1-yl)tetrafluorobenzyl 3-(2-chloro-3,3,3-trifluoroprop-1-en-1-yl)-2,2-dimethylcyclopropane carboxylate (compound no. 21, Table I) in the form of a mixture of 50% of the E-butenyl and 50% of the Z-butenyl isomeric forms of the (±)-cis isomeric form (with respect the cyclopropane ring).

Product X: 4-allyl-2,6-difluorobenzyl 3-(2-chloro-3,3,3-trifluoroprop-1-en-1-yl)-2,2-dimethylcyclopropane carboxylate (compound no. 30, Table II) in its (±)-cis isomeric form.

Product Y: 4allyl-3,5-difluorobenzyl 3-(2-chloro-3,3,3-trifluoroprop-1-en-1-yl)-2,2-dimethylcyclopropane carboxylate (compound no. 29, Table II) in its (±)-cis isomeric form.

Product Z: 4-benzyltetrafluorobenzyl 3-(2-chloro-3,3,3-trifluoroprop-1-en-1-yl)-2,2-dimethylcyclopropane carboxylate (compound no. 22, Table I) in its (±) isomeric form.

The compounds of formula I may be used to combat and control infestations of insect pests and also other invertebrate pests, for example, acarine pests. The insect and acarine pests which may be combatted and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise a insecticide synergist, such as for example imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Aphis fabrae* (aphids)
*Megoura visceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back month, larvae)
*Phaedon cochleariae* (Mustard beetle)
*Telarius cinnabarinus* (carmine spider mite)
*Aonidiella spp.* (scale insects)
*Trialeuroides spp.* (white flies)
*Blattella germanica* (cockroaches)
*Spodoptera littoralis* (cotton leaf worm)
*Chortiocetes terminifera* (locusts)
*Diabrotica spp.* (rootworms)
*Agrotis spp.* (cutworms)

The compounds of formula I and compositions comprising them have shown themselves to be particularly useful in controlling lepidopteran pests of cotton, for example *Spodoptera spp.* and *Heliothis spp.* The fumigant properties of the compound enable them to be used to combat pests which inhabit the soil, for example *Diabrotica spp.* They are also excellent knock down agents and as such may be used in conjunction with other insecticides to combat public health pests such as flies. They are also very useful in combatting insect and acarine pests which infest domestic animals, such as *Lucilia sericata*, land ixodid ticks such as *Boophilus spp., Ixodes spp., Amblyomma spp., Rhipicephalus spp.*, and *Dermaceutor spp.* They are effective in combatting both susceptible and resistant strains of these pests in their adult, larval and intermediate stages of growth, and may be applied to the infested host animal by topical, oral or parenteral administration.

The following Examples illustrate the various aspects of the invention.

EXAMPLE 1

This Example illustrates the insecticidal properties of the Products A to Z.

The activity of the products was determined using a variety of insect pests. The product was used in the form of liquid preparations containing 500, 100, 50 or 25 parts per million (p.p.m.) by weight of the product. The preparations were made by dissolving the product in a mixture of solvents consisting of 4 parts by volume of acetone and 1 part by volume of diacetone alcohol. The solutions were then diluted with water containing 0.01% by weight of a wetting agent sold under the trade name "LISSAPOL" until the liquid preparations contained the required concentration of the product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment. Details are given in Table III.

The results of the tests are given in Table IV for each of the products A to Z at the rate in parts per million given in the second column as a grading of mortality on a scale of 0-9 wherein

```
0 represents less than 10% mortality
1 represents from 10 to 19% mortality
2 represents from 20 to 29% mortality
3 represents from 30 to 39% mortality
4 represents from 40 to 49% mortality
5 represents from 50 to 59% mortality
6 represents from 60 to 69% mortality
7 represents from 70 to 79% mortality
8 represents from 80 to 89% mortality
9 represents from 90 to 100% mortality
```

In Table IV the pest organism used is designated by a letter code and the pest species, the support medium or food, and the type and duration of test is given in Table III.

TABLE IV

| PRODUCT | RATE (ppm) | MD | SL | PX | SG | DB |
|---|---|---|---|---|---|---|
| A | 50 | 9 | 9 | 9 | 9 | 9 |
| B | 100 | 0 | 9 | 9 | 0 | 9 |
| C | 100 | 9 | 9 | 9 | 0 | 9 |
| D | 500 | 9 | 9 | 9 | 7 | 9 |
| E | 100 | 9 | 9 | 9 | 9 | 9 |
| F | 50 | 9 | 9 | 9 | 9 | 9 |
| G | 50 | 9 | 9 | 9 | 0 | 9 |
| H | 50 | 9 | 9 | 9 | 0 | 9 |
| J | 50 | 9 | 9 | 9 | 0 | 9 |
| K | 50 | 9 | 9 | 9 | 9 | 9 |
| L | 50 | 9 | 9 | 9 | 9 | 9 |
| M | 100 | 9 | 9 | 9 | 8 | 9 |
| N | 500 | 9 | 9 | 9 | 7 | 9 |
| O | 100 | 9 | 9 | 9 | 0 | 9 |
| P | 25 | 9 | 9 | 9 | 5 | 9 |
| Q | 100 | 9 | 9 | 9 | 9 | 9 |
| R | 50 | 9 | 9 | 9 | 9 | 9 |
| S | 50 | 9 | 9 | 9 | 9 | 9 |
| T | 50 | 9 | 9 | 9 | 9 | 9 |
| U | 50 | 9 | 9 | 9 | 9 | 9 |
| V | 100 | 9 | 9 | 9 | 0 | 9 |
| W | 50 | 9 | 9 | 9 | 9 | 9 |
| X | 50 | 9 | 8 | 9 | 9 | 9 |
| Y | 50 | 9 | 9 | 9 | 9 | 9 |
| Z | 500 | 0 | 9 | 9 | 9 | 9 |

In further tests the products showed insecticidal activity against a number of other species. Thus for example Products B,C and E showed aphicidal properties against *Aphis fabae*.

In Table V below the minimum concentration (in parts per million) required to give 100% mortality of red spider mite adults (*Tetranychus telarius*, SM) on French bean leaves and plant hoppers (*Nilaparvata lugens*, PH) on rice is given for several of the Products. A dash (-) in this table indicates that 100% mortality was not obtained at the highest rate tested (usually 500 parts per million).

TABLE V

| Product | Rate (ppm) giving 100% mortality | | Product | Rate (ppm) giving 100% mortality | |
|---|---|---|---|---|---|
| | SM | PH | | SM | PH |
| C | 100 | 100 | R | — | 500 |
| E | 100 | 100 | S | 50 | 50 |
| K | — | 500 | U | 50 | 50 |
| L | — | 100 | V | — | — |
| M | 500 | 500 | W | — | 50 |
| N | — | 500 | X | 100 | 50 |
| O | — | 500 | Y | — | 100 |
| Q | 500 | 500 | Z | — | 500 |

TABLE III

| CODE LETTERS (Table IIB) | PEST SPECIES | SUPPORT MEDIUM/FOOD | TYPE OF TEST* | DURATION (days) |
|---|---|---|---|---|
| MD | *Musca domestica* (houseflies - adults) | Cotton wool/milk, sugar | Contact | 2 |
| SL | *Spodoptera littoralis* (cotton leaf worm - larvae) | Cotton leaves | Residual | 1 |
| PX | *Plutella xylostella* (diamond back moth - larvae) | Mustard leaves | Residual | 3 |
| SG | *Sitophilus granarius* (grain weevil - adults) | Grain | Contact | 3 |
| DB | *Diabrotica balteata* (rootworm - larvae) | Filter paper | Contact | 3 |

*"Contact" test indicates that both pests and medium were treated and "residual" indicates that the medium was treated before infestation with the pests.

EXAMPLE 2

This Example illustrates the preparation of 2-methyl-3,4,5,6-tetrafluorobenzyl alcohol.

(a) Preparation of 2,3,4,5-tetrafluorotoluene.

A solution of n-butyllithium in hexane (1.6 M, 62.5 ml) was added dropwise to a well stirred solution of 1,2,3,4-tetrafluorobenzene (15.0 g) in dry tetrahydrofuran (150 ml) maintained at a temperature of $-60°$ under an atmosphere of dry argon. When the addition was complete the mixture was stirred at $-45°$ C. for 2 hours and then methyl iodide (14.2 g) was added dropwise whilst the temperature was kept at $-45°$ C. After a period of 30 minutes the mixture was allowed to warm to the ambient temperature, poured into distilled water and the mixture extracted with diethyl ether ($2 \times 50$ ml), and the extracts dried over anhydrous magnesium sulphate. After filtering the solution was concentrated by evaporation of the solvents at atmospheric pressure. The residual oil was distilled and the fraction boiling in the range $115°$-$122°$ C. at atmospheric pressure (6.2 g) collected, identified by n.m.r. and gas chromatographic analysis as consisting of ca. 90% of the required 2,3,4,5-tetrafluorotoluene and ca. 10% of 3,4,5,6-tetrafluoro-1,2-xylene.

(b) Preparation of 3,4,5,6-tetrafluoro-2-toluic acid.

The product of step (a) above (5.5g) was mixed with diethyl ether (35 ml), the mixture cooled to $-70°$ C., and maintained at this temperature whilst a solution of n-butyllithium in h-hexane (1.6 M, 21 ml) was slowly added. The mixture was stirred for a period of 1 hour during which time a fine white precipitate was formed. Dry carbon dioxide gas was then passed into the mixture for 30 minutes whilst the temperature was maintained within the range $-70°$ to $-40°$ C., and continued to be passed in thereafter whilst the mixture was allowed to warm to the ambient temperature.

After acidifying with dilute hydrochloric acid (6N, 40 ml) the organic phase was separated, washed with water and dried over anhydrous magnesium sulphate. After evaporation of the solvents under reduced pressure the residual oil (which from n.m.r. analysis was shown to be an approximately 1:1 mixture of the desired product and pentanoic acid) was carefully distilled under reduced pressure (water pump) using a Kugelrohr apparatus, and the fraction which solidified on cooling collected and recrystallised from toluene to yield 3,4,5,6-tetrafluoro-2-toluic acid, m.p. $165°$ C. (0.65 g), identified by infra red and nuclear magnetic resonance spectroscopy.

(c) Preparation of 2-methyl-3,4,5,6-tetrafluorobenzyl alcohol.

3,4,5,6-tetrafluoro-2-toluic acid (500 mg) was dissolved in dry diethyl ether (5.0 ml) added dropwise to a suspension of lithium aluminium hydride (100 mg) in dry ether (10 ml) under an argon atmosphere at the ambient temperature. When the addition was complete and the effervescence has subsided the mixture was heated at the reflux temperature for a period of 1 hour. After allowing the mixture to cool to the ambient temperature water (10 ml) was cautiously added and the resultant mixture extracted with diethyl ether ($2 \times 20$ ml), the extracts washed with water and dried over anhydrous magnesium sulphate. After filtration the filtrate was concentrated by evaporation of the solvent. The residual low melting solid was recrystallised from petroelum ether (boiling range $40°$-$60°$ C.) to yield 2-methyl-3,4,5,6-tetrafluoro-benzyl alcohol (200 mg).

N.m.r. ($^1$H(ppm)CDCl$_3$): 2.18(s,1H); 2.32(t,3H); 4.86(s,2H).

EXAMPLE 3

The procedures of Example 2 were used to prepare various benzyl alcohols from tetrafluorobenzenes via the appropriate benzoic acids.

(a) By the procedure set out in paragraph (a) of Example 2 (but using the appropriate lithium derivatives) the following conversions were effected:

(a) (i) 1,2,4,5-tetrafluorobenzene to 2,3,5,6-tetrafluorotoluene (b.p. $117°$-$121°$ C., contaminated with ca 5% 2,3,5,6-tetrafluoroxylene).

N.m.r. ($^1$H(ppm)CDCl$_3$): 2.28(t, 3H); 6.58–6.94 (m, 1H). Infra red (liquid film): 3075, 1645, 1510, 1255, 1165 cm$^{-1}$.

(ii) 1,2,4,5-tetrafluorobenzene to ethyl-2,3,5,6-tetrafluorobenzene (b.p. $128°$-$134°$ C.).

N.m.r. ($^1$H(ppm)CDCl$_3$): 1.20 (t,3H); 2.72 (q, 2H); Infra red (liquid film): 3075, 1650, 1510, 1250 cm$^{-1}$.

(iii) 1,2,4,5-tetrafluorobenzene to n-propyl-2,3,5,6-tetrafluorobenzene (b.p. $142°14$ $146°$ C.).

N.m.r. ($^1$H(ppm)CDCl$_3$): 0.96 (t, 3H); 1.64 (q, 2H); 2.74 (t, 2H); 6.74–7.08 (m, 1H).

Infra red (liquid film): 3075, 1655, 1495, 1255 cm$^{-1}$.

(iv) 1,2,4,5-tetrafluorobenzene to benzyl-2,3,5,6-tetrafluorobenzene (m.p. $38°$-$40°$ C.)

N.m.r. ($^1$H(ppm)CDCl$_3$): 4.02 (s, 2H); 6.68–7.08 (m, 1H); 7.20 (s, 5H).

Infra red (liquid paraffin): 3080, 1645, 1605, 1500 1250 cm$^{-1}$.

(v) 1,2,4,5-tetrafluorobenzene to allyl-2,3,5,6-tetrafluorobenzene

N.m.r. ($^1$H(ppm)CDCl$_3$): 3.40 (m, 2H); 4.78–5.18 (m, 2H); 5.60–6.05 (m,1H); 6.60–7.00 (m,1H).

Infra red (liquid film): 3080, 1640, 1500, 1250, 1170, 850 cm$^{-1}$.

(b) By the use of the procedure set out in paragraph (b) of Example 2 the following benzoic acids were obtained from the appropriate precursor as follows:

(i) 4-methyl-2,3,5,6-tetrafluorobenzoic acid (from 2,3,5,6-tetrafluorotoluene)—m.p. $170°$ C.

N.m.r. ($^1$H(ppm)CDCl$_3$): 2.44(t,3H); 11.56 (s,1H).

Infra red (liquid paraffin): 3300–2450, 1710, 1650, 1460, 1070 cm$^{-1}$.

(ii) 4-ethyl-2,3,5,6-tetrafluorobenzoic acid (from ethyl-2,3,5,6-tetrafluorobenzene)—m.p. $92°$-$93°$ C.

N.m.r. ($^1$H(ppm)CDCl$_3$): 1.24 (t,3H); 2.80 (q,2H) 13.30 (s,1H).

Infra red (liquid paraffin): 3300–2450, 1710, 1650, 1485, 1460, 965 cm$^{-1}$.

(iii) 4-n-propyl-2,3,5,6-tetrafluorobenzoic acid (from n-propyl 2,3,5,6-tetrafluorobenzene)—m.p. $65°$-$68°$ C.

N.m.r. ($^1$H(ppm)CDCl$_3$): 0.98 (t,3H); 1.68 (q,2H); 2.76 (t,2H); 11,34 (s,1H)

Infra red (liquid paraffin): 3300–2450, 1710, 1650, 1485, 1450 cm$^{-1}$.

(iv) 4-benzyl-2,3,5,6-tetrafluorobenzoic acid (from benzyl-2,3,5,6-tetrafluorobenzene)—m.p. $161°$-$164°$ C.

N.m.r. ($^1$H(ppm)CDCl$_3$): 4.06 (s,2H); 7.22 (s,5H); 10.06 (s,1H).

Infra red (liquid paraffin): 3300–2450, 1705, 1650, 1485, 1005 cm$^{-1}$.

(v) 4-allyl-2,3,5,6-tetrafluorobenzoic acid (from allyl-2,3,5,6-tetrafluorobenzene)—m.p. $88°$-$90°$ C.

N.m.r. ($^1$H(ppm)CDCl$_3$): 3.50 (m,2H); 4.95–5.20 (m,2H); 5.60–6.08 (m,1H); 11.82 (s,1H).

Infra red (liquid paraffin): 3300–2300, 1700, 1650, 1470, 1410, 1290, 1240, 980 cm$^{-1}$.

(c) By the procedure set out in paragraph (c) of Example 2 the benzyl alcohols were obtained by reduction of the appropriate acids as follows:
(i) 4-methyl-2,3,5,6-tetrafluorobenzyl alcohol (from 4-methyl-2,3,5,6-tetrafluorobenzoic acid)—m.p. 61°–62° C.

N.m.r. ($^1$H(ppm)CDCl$_3$): 2.24 (t,3H); 2.06 (s,1H) 4.82 (s,2H).

Infra red (liquid paraffin): 3300–1660, 1460, 1280, 1020 cm$^{-1}$.

(ii) 4-ethyl-2,3,5,6-tetrafluorobenzyl alcohol (from 4-ethyl-2,3,5,6-tetrafluorobenzoic acid)—m.p. 36°–37° C.

N.m.r. ($^1$H(ppm)CDCl$_3$): 1.22 (t,3H); 2.06 (s,1H); 2.76 (q,2H); 4.78 (s,2H).

Infra red (liquid paraffin): 3300, 1660, 1490, 1465, 1280 cm$^{-1}$.

(iii) 4-n-propyl-2,3,5,6-tetrafluorobenzyl alcohol (from 4-n-propyl-2,3,5,6-tetrafluorobenzoic acid).

N.m.r. ($^1$H(ppm)CDCl$_3$): 0.94 (t,3H); 1.60 (q,2H); 2.12 (s,1H); 2.66 (t,2H); 4.70 (s,2H).

Infra red (liquid film): 3350, 1660, 1485, 1280, 1015 cm$^{-1}$.

(iv) 4-benzyl-2,3,5,6-tetrafluorobenzyl alcohol (from 4-benzyl-2,3,5,6-tetrafluorobenzoic acid)—m.p. 72°–74° C.

N.m.r. ($^1$H(ppm)CDCl$_3$): 2.00 (s,1H); 4.04 (s,2H); 4.78 (s,2H); 7.22 (s,5H).

Infra red (liquid paraffin): 3300, 1655, 1485, 1010 cm$^{-1}$.

(v) 4-allyl-2,3,5,6-tetrifluorobenzyl alcohol (from 4-allyl-2,3,5,6-tetrafluorobenzoic acid).

N.m.r. ($^1$H(ppm)CDCl$_3$): 2.42 (s,1H); 3.35 (m,2H); 4.68 (m,2H); 4.82–5.10 (m,2H); 5.55–5.98 (m,1H).

Infra red (liquid film): 3600–3100, 2950, 1640, 1490, 1300, 1270, 1020, 860 cm$^{-1}$.

EXAMPLE 4

This Example illustrates the preparation of 4-methoxy-2,3,5,6-tetrafluorobenzyl alcohol.

Pentafluorobenzyl alcohol (1.98 g) was added to a stirred solution of sodium methoxide (obtained by dissolving sodium (0.4 g) in methyl alcohol (10 ml) at the ambient temperature, and the mixture heated at the reflux temperature for 3.5 hours. After cooling the mixture, the solvent was removed by evaporation under reduced pressure and the residue partitioned between water and diethyl ether. After separating the ethereal layer and washing with water, it was dried over anhydrous magnesium sulphate and concentrated by evaporation of the solvent under reduced pressure to yield 4-methoxy-2,3,5,6-tetrafluorobenzyl alcohol (1.8 g), identical with the product of Example 5.

Infra red (liquid film): 3600–3100, 2950, 1650, 1500, 1200, 1130, 1040, 1000, 930 cm$^{-1}$.

EXAMPLE 5

This Example illustrates the preparation of 4-methoxy-2,3,5,6-tetrafluorobenzyl alcohol.

(a) Preparation of pentafluorobenzyl tetrahydropyran-2-yl ether.

A mixture of pentafluorobenzyl alcohol (17.87 g) 2,3-dihydro-4H-pyran (8.3 g), dry diethyl ether (100 ml) and concentrated hydrochloric acid (0.2 ml) was stirred at the ambient temperature for 4 hours, after which the mixture was washed with water, dried over anhydrous magnesium sulphate and concentrated by evaporation under reduced pressure. The residual oil was identified by infra red spectroscopy as pentafluorobenzyl tetrahydropyran-2-yl ether.

(b) Preparation of 4-methoxy-2,3,5,6-tetrafluorobenzyl tetrahydropyran-2-yl ether.

To a mixture of freshly prepared dry sodium methoxide (obtained by dissolving sodium metal (0.46 g) in dry methyl alcohol and evaporating to dryness) and dry pyridine (25 ml) was added, dropwise with vigorous stirring, a solution of pentafluorobenzyl tetrahydropyran-2-yl ether (2.82 g) in dry pyridine (20 ml), and the resultant mixture stirred for 3.5 hours and then allowed to stand at the ambient temperature for 16 hours. The mixture was poured into water, acidified with dilute hydrochloric acid, and extracted with chloroform. After drying the extracts with anhydrous magnesium sulphate, the solvents were evaporated under reduced pressure and the residual pressure and the residual oil identified by n.m.r. and infra red spectroscopy as 4-methoxy-2,3,5,6-tetrafluorobenzyl tetrahydropyran-2-yl ether.

(c) Preparation of 4-methoxy-2,3,5,6-tetrafluorobenzyl alcohol.

The product of step (b) above (2.8 g) was dissolved in a mixture of methyl alcohol (50 ml) and concentrated hydrochloric acid (4 ml) and the resultant mixture heated at reflux temperature for a period of 5 hours. After removal of the methanol by evaporation under reduced pressure the residual oil was partitioned between water and chloroform. The chloroform layer was separated, washed with water, dried over anhydrous magnesium sulphate, and concentrated by evaporation of the chloroform to yield 4-methoxy-2,3,5,6-tetrafluorobenzyl alcohol as a colourless oil. The identity was confirmed by n.m.r. and infra red spectroscopy.

N.m.r. ($^1$H(ppm)CDCl$_3$): 2.63 (s,1H); 4.02 (d,3H); 4.65 (d,2H).

EXAMPLE 6

By the procedure illustrated in Example 5 4-ethylthio-2,3,5,6-tetrafluorobenzyl alcohol (b.p. 120° C./0.05 mm Hg. Kugelrohr apparatus) was obtained from pentafluorobenzyl tetrahydropyran-2-yl ether via 4-ethylthio-2,3,5,6-tetrafluorobenzyl tetrahydropyran-2yl ether.

N.m.r. ($^1$H(ppm)CDCl$_3$): 1.24 (t,3H); 2.70 (s,1H); 2.94 (q,2H); 4.73 (s,2H).

EXAMPLE 7

This Example illustrates the preparation of 4-ethanesulphonyl-2,3,5,6-tetrafluorobenzyl alcohol.

A mixture of 4-ethylthiotetrafluorobenzyl tetrahydropyran-2yl ether (1.4 g), hydrogen peroxide (30% w/v, 100 vol, 4 ml) and glacial acetic acid (25 ml) was heated at the reflux temperature for 6 hours, kept at the ambient temperature for 16 hours and then heated at the reflux temperature for 4 hours. The mixture was cooled, diluted with water, and extracted with chloroform.

The extracts were washed with satureated sodium bicarbonate solution, dried over anhydrous magnesium sulphate and concentrated by evaporation of the solvent under reduced pressure. The residual oil (believed to be 4-ethanesulphonyltetrafluorobenzyl tetrahydropyran-2-yl ether) was dissovled in a mixture of methanol (30 ml) and concentrated hydroxhloric acid (3.0 ml) and heated at the reflux temperature for 5 hours. After removal of the volatile portion by evaporation under reduced pressure the residue was partitioned between water and chloroform, the chloroform layer washed with water, dried over anhydrous magnesium sulphate and concentrated under reduced pressure to yield 4-ethanesulphonyltetrafluorobenzyl alcohol, identified by infra red and n.m.r. spectroscopy.

N.m.r. ($^1$H(ppm)CDCl$_3$): 1.40 (t,3H); 3.21 (s,1H); 3.42 (q,2H); 4.85 (s,2H).

EXAMPLE 8

The procedure of Example 4 was used to prepare 4-allyloxy-2,3,5,6-tetrafluorobenzyl alcohol by the reaction of pentafluorobenzyl alcohol with a solution of sodium in allyl alcohol.

N.m.r. ($^1$H(ppm)CDCl$_3$): 3.20 (s,1H); 4.70 (t,4H); 5.18–5.54 (m,2H); 5.81–6.22 (m,1H).

Infra red (liquid film): 3600–3100, 2950, 1650, 1495, 1420, 1140, 1030, 980, 930 cm$^{-1}$.

EXAMPLE 9

This Example illustrates the preparation of 4-(3-methyl-but-2-en-1-yl)-2,3,5,6-tetrafluorobenzyl alcohol.

(a) 2,3,5,6-tetrafluorobenzyl alcohol.

Lithium aluminium hydride (4.6 g) was added in small portions to a stirred solution of 2,3,5,6-tetrafluorobenzoic acid (30.0 g) in dry ether (600 ml) at the ambient temperature, and stirring continued for a period of 3 hours. After decomposition of the excess lithium aluminium hydride with ethyl alcohol, water was added in excess and the ethereal phase separated, washed with water, and concentrated to yield crude 2,3,5,6-tetrafluorobenzyl alcohol (13.0 g) as a colourless oil.

N.m.r. ($^1$H(ppm)CDCl$_3$): 3.44 (s,1H); 4.72 (t,2H); 6.80–7.40 (m,1H).

Infra red (liquid film): 3600–3100, 2950, 1510, 1260, 1180, 1050, 870 cm$^{-1}$.

(b) 2,3,5,6-tetrafluorobenzyl tetrahydropyranyl ether was prepared from the product of step (a) by the method set out in step (a) of Example 5.

N.m.r. ($^1$H(ppm)CDCl$_3$): 1.30–2.10 (m,6H); 3.40–4.10 (m,2H); 4.45–5.10 (m,3H); 6.86–7.32 (m,1H).

Infra red (liquid film): 2950, 1510, 1270, 1175, 1120, 1030 970, 870 cm$^{-1}$.

(c) 4-methylbut-2-en-1-yl)-2,3,5,6-1-tetrafluorobenzyl tetrahydropyranyl ether.

The product from step (b) (0.84 g) was dissolved in dry tetrahydrofuran and then stirred solution cooled to −70° C. under an argon atmosphere. Lithium butyl (2.2 ml of a 1.6 M solution in n-hexane was added slowly, after which the resultant mixture was stirred for 45 minutes at −70° C. 1-bromo-3-methylbut-2-ene (0.50 ml of a freshly distilled sample) was added slowly and after a further 30 minutes stirring at −70° C. the mixture was allowed to attain the ambient temperature (ca. 25° C.). Water was carefully added to the mixture which was then acidified with dilute hydrochloric acid. After keeping for 18 hours the ethereal phase was separated from the mixture, the aqueous phase extracted with diethyl ether and the extract combined with the ethereal phase. After washing with water and drying over anhydrous magnesium sulphate the ethereal solution was concentrated by evaporation of the solvents under reduced pressure and the residual oil (0.85 g) identified as a mixture of the required product with the starting material.

Infra red (liquid film): 2950, 1510, 1490, 1270, 1175, 1120, 1030, 970, cm$^{-1}$.

(d) 4-methylbut-2-en-1yl)-2,3,5,6-tetrafluorobenzyl alcohol was obtained (in mixture with 2,3,4,5-tetrafluorobenzyl alcohol) by subjecting the mixture prepared in step (c) to the method of step (c) of Example 5. The required product was separated from the mixture by thick layer preparative chromatography using 2 mm thick silica gel plates and ether/chloroform (1:10 by volume) as eluent.

N.m.r. ($^1$H(ppm)CDCl$_3$): 1.72 (d,6H; 2.72 (m,1H); 3.41 (m,2H); 4.80 (s,2H); 5.07–5.35 (m,1H).

Infra red (liquid film): 3600–3100, 2990, 1500, 1260, 1180 1090, 870 cm$^{-1}$.

EXAMPLE 10

The procedures of Example 9 were used to prepare other 4-alkenylfluorobenzyl alcohols via their tetrahydropyranyl ethers as follows:

(i) 4-(but-3-en-1-yl)-2,3,5,6-tetrafluorobenzyl alcohol.

N.m.r. ($^1$H(ppm)CDCl$_3$): 1.48–1.78 (m,3H); 2.60 (s,1H) 3.40 (m,2H); 4.70 (s,2H); 5.25–5.75 (m,2H).

Infra red (liquid film): 3600–3100, 1495, 1275, 1030 975, 860 cm$^{-1}$.

(ii) 4-(but-3-en-1yl)-2,4,5,6-tetrafluorobenzyl tetrahydropyranyl ether (mixture with 2,3,5,6-tetrafluorobenzyl tetrahydropyranyl ether).

Infra red (liquid film): 2950, 1505, 1490, 1260, 1200, 1120, 1030, 970, 910, 870 cm$^{-1}$.

(iii) 4-allyl-3,5-difluorobenzyl alcohol

N.m.r. ($^1$H(ppm)CDCl$_3$): 2.10 (m,1H); 3.40 (m,2H); 4.62 (s,2H); 4.90–5.15 (m,2H); 5.68–6.18 (m,1H); 6.85 (m,2H).

Infra red (liquid film): 3600–3100, 2950, 1640, 1585, 1435, 1315, 1215, 1190, 1115, 1030 cm$^{-1}$.

(iv) 4-allyl-3,5-difluorobenzyl tetrahydropyranyl ether (mixture with 3,5-difluorobenzyl tetrahydropyranyl ether).

Infra red (liquid film): 2950, 1640, 1595, 1585, 1435, 1200, 1115, 1070, 1030, 1000, 905 cm$^{-1}$.

(v) 3,5-difluorobenzyl alcohol—b.p. 200°–202° C. Infra red (liquid film): 3600–3100, 2900, 1625, 1595 1460, 1320, 1115, 955, 850 cm$^{-1}$

EXAMPLE 11

This Example illustrates the preparation of 4-allyl-2,6-difluorobenzyl alcohol.

(a) Allyl-3,5-difluorobenzene

A solution of allyl bromide (2.5 g) in dry tetrahydrofuran (10 ml) was added dropwise with stirring to 3,5-difluorobromobenzene (4.0 g) with magnesium (0.5 g) in dry tetrahydrofuran (40 ml), whilst maintaining the temperature of the mixture at about 20° C. When the addition was complete the mixture was allowed to warm to the ambient temperature (ca. 25° C.). After a period of 18 hours the mixture was poured into water (100 ml) and the resultant mixture extracted with diethyl ether, the extract washed with water, dried over anhydrous magnesium sulphate and the ether removed by distillation at atmospheric pressure. The residual oil was purified by distillation at atmospheric pressure to yield allyl-3,5-difluorobenzene (b.p. 154°–155°) as a colourless oil.

N.m.r. ($^1$H(ppm)CDCl$_3$): 3.40 (d,2H); 5.10 (dd,2H); 6.00 (m,1H); 6.70 (m,3H).

(b) 4-allyl-3,5-difluorobenzoic acid was obtained from the product of step (a) by using the procedure of step (b) of Example 2, as a white solid, m.p 80°–82° C.

N.m.r. ($^1$H(ppm)CDCl$_3$): 3.40 (d,2H); 5.20 (dd,2H); 6.00 (m,1H); 6.90 (d,2H); 10.90 (s,1H).

Infra red (liquid paraffin): 3300–2500, 1700, 1630, 1570, 1450, 1280, 1040, 930 cm$^{-1}$.

(c) 4-Allyl-3,5-difluorobenzyl alcohol was obtained by the reduction of the product of step (b) by the use of the procedure of step (c) of Example 2.

N.m.r. ($^1$H(ppm)CDCl$_3$): 3.40 (d,3H); 4.70 (s,2H); 5.20 (dd,2H); 6.00 (m,1H); 6.8 (d,2H).

EXAMPLE 12

This Example illustrates the preparation of 3-methyl-2,4,5,6-tetrafluorobenzyl alcohol.

(a) 3-bromo-2,4,5,6-tetrafluorotoluene.

A solution of dimethyl sulphate (8.0 ml) in dry tetrahydrofuran (20 ml) was added slowly to a stirred solution of 3-bromotetrafluorobenzene magnesium bromide [obtained by the reaction of magnesium (1.6 g) with 1,3-dibromotetrafluorobenzene (20 ml)] in dry tetrahydrofuran (150 ml) over 30 minutes at the ambient temperature. When the addition was complete the mixture temperature had risen to 45° C. The mixture was heated at the reflux temperature for 15 minutes and then cooled to the ambient temperature (ca. 25° C.). Dilute hydrochloric acid (30 ml of a 1N solution) was added and the mixture thereafter neutralised with saturated sodium bicarbonate solution. After diluting the mixture with water (200 ml) it was extracted with ether and the extracts washed with water and dried over anhydrous magnesium sulphate. After removal of the solvent by evaporation under reduced pressure the residual oil was distilled to yield 3-bromo-2,4,5,6-tetrafluorotoluene (9.0 g), b.p. 96°–98° C. 85 mm Hg.

(B) 3-methyl-2,4,5,6-tetrafluorobenzaldehyde n-Butyl lithium (12.9 ml of a 1.6M solution in hexane) was added dropwise to a solution of 3-bromo-2,4,5,6-tetrafluorotoluene (5.0 g) in diethyl ether (40 ml) under an argon atmosphere whilst maintaining the mixture temperature within the range −60° to −70° C. When the addition was complete the mixture was stirred for a period of 1.5 hours at −70° C. after which a solution of N-methylformanilide (2.8 g) in diethyl ether (15 ml) was added and the resultant mixture allowed to attain the ambient temperature (ca. 25° C.). Dilute hydrochloric acid (25 ml) of a 2N solution was added to the well-stirred mixture after which the ethereal layer was separated, washed with water and dried over anhydrous magnesium sulphate. After removal of the solvent by evaporation under reduced pressure the residual oil was distilled to yield 3-methyl-2,4,5,6-tetrafluorobenzaldehyde (1.6 g) b.p. 78°–80° C./14 mm Hg.

Infra red (liquid film); 1710, 1640, 1490, 1140 cm$^{-1}$.

(c) 3-Methyl-2,4,5,6-tetrafluorobenzaldehyde.

Sodium borohydride (0.3 g) was added in small portions to a solution of 3-methyl-2,4,5,6-tetrafluorobenzaldehyde (1.5 g) in methyl alcohol (15 ml) at the ambient temperature, after which the mixture was heated at the reflux temperature for 30 minutes. The methyl alcohol was removed by evaporation under reduced pressure and the residue partitioned between dilute hydrochloric acid (20 ml of a 0.1N solution) and ether (20 ml). The ethereal phase was separated, washed with saturated sodium bicarbonate solution and with water and then dried over anhydrous magnesium sulphate. After evaporation of the ether under reduced pressure the product was distilled in a Kugelrohr apparatus to yield 3-methyl-2,4,5,6-tetrafluorobenzyl alcohol (1.2 g)—approximate b.p. 100° C./14 mm Hg.

N.m.r. ($^1$H(ppm)CDCl$_3$): 2.20 (s,3H); 3.20 (t,1H); 4.6 (m,2H).

Infra red (liquid film): 3300, 1650, 1480, 1120, 1110 cm$^{-1}$.

EXAMPLE 13

This Example illustrates the preparation of 4-ethylthio-2,3,5,6-tetrafluorobenzyl 3-(2-chloro-3,3,3-trifluoroprop-1-en-1-yl)-2,2-dimethylcyclopropane carboxylate (compound no. 2, Table I) consisting of 50% w/w of the (±)-cis isomer and 50% w/w of the (±)-trans isomer (Product B).

A mixture of thionyl chloride (5.0 ml) and 3-(2-chloro-3,3,3-trifluoroprop-1-en-1-yl)-2,2-dimethylcyclopropane carboxylic acid (50% cis, 50% trans (w/w), 0.242 g) was heated at the reflux temperature for 5 hours, and then kept at the ambient temperature for 16 hours. After removing the excess thionyl chloride by evaporation under reduced pressure (the last traces being removed by azeotropic distillation with toluent) the resultant acid chloride was added to a mixture of 4-ethylthiotetrafluorobenzyl alcohol (0.24 g), dry pyridine (0.08 g) and dry toluene (10 ml), and the resultant mixture stirred at the ambient temperatures for 2 hours and then stood at the ambient temperature for a further 16 hours. After adding toluene (10 ml) the mixture was washed successively with dilute hydrochloric acid (2N, 20 ml), water and saturated sodium bicarbonate solution, dried over anhydrous magnesium sulphate and concentrated by evaporation of the solvent under reduced pressure yielding, as a residual oil, 4-ethylthio-2,3,5,6-tetrafluorobenzyl 3-(2-chloro-3,3,3-trifluoroprop-1-en-1-yl)-2,2-dimethylcyclopropane carboxylate, identified by n.m.r. and infra red spectroscopy.

N.m.r. ($^1$H(ppm)CDCl$_3$): 1.16–1.38 (m,9H); 1.71–2.50 (m,2H); 2.97 (q,2H); 5.19 (2s,2H); 6.08, 6.82 (2d,1H).

EXAMPLE 14

By the use of the procedure set out in Example 13 above the following Products were prepared from the stated acids and alcohols, and identified by their n.m.r. and infra red spectra.

Product A from 4-methyl-2,3,5,6-tetrafluorobenzyl alcohol and 3-(2-chloro-3,3,3-trifluoroprop-1-en-1-yl)-2,2-dimethyl-cyclopropane carboxylic acid (50% cis, 50% trans, w/w).

N.m.r. ($^1$H(ppm)CDCl$_3$): 1.24–1.44 (m,6H); 1.70–2.58 (m,2H); 2.28 (t,3H); 5.20–5.28 (2s,2H); 6.12 6.90 (2d,1H).

Product C from 4-methyl-2,3,5,6-tetrafluorobenzyl alcohol and 3-(2,2-dichlorovinyl)-2,2-dimethylcyclopropane carboxylic acid (50% cis, 50% trans, w/w).

N.m.r. ($^1$H(ppm)CDCl$_3$): 1.24–1.40 (m,6H); 1.56–2.36 (m,2H); 2.28 (t,3H); 5.20–5.28 (2s,2H); 5.58 6.22 (2d,1H).

Product D from 4-ethanesulphonyl-2,3,5,6-tetrafluorobenzyl alcohol and 3-(2-chloro-3,3,3-trifluoroprop-1-en-1-yl)-2,2-dimethylcyclopropane carboxylic acid (50% cis, 50% trans, w/w).

N.m.r. ($^1$H(ppm)CDCl$_3$): 1.19–1.52 (m,9H); 1.68–2.49 (m,2H); 3.31 (q,2H); 5.19 (2s,2H); 6.07, 6.77 (2d,1H).

Product E from 4-methoxy-2,3,5,6-tetrafluorobenzyl alcohol and 3-(2-chloro-3,3,3-trifluoroprop-1-en-1-yl)-2,2-dimethylcyclopropane carboxylic acid (50% cis, 50% trans, w/w).

N.m.r. ($^1$H(ppm)CDCl$_3$): 1.15–1.38 (m,6H); 1.65–2.50 (m,2H); 4.00 (d,3H); 5.10 (m,2H) 6.04, 6.78 (2d,1H).

Product F from 2-methyl-3,4,5,6-tetrafluorobenzyl alcohol and 3-(2-chloro-3,3,3-trifluoromethylprop-1-en- 1-yl)-2,2-dimethylcyclopropane carboxylic acid (50% cis, 50% trans, w/w).

N.m.r. ($^1$H(ppm)CDCl$_3$): 1.24–1.40 (m,6H); 1.72–2.52 (m,2H) 2.30 (t,3H); 5.10–5.20 (2s,2H); 6.10, 6.82 (2d,1H).

Product G from 4-ethoxy-2,3,5,6-tetrafluorobenzyl alcohol and 3-(2-chloro-3,3,3-trifluoroprop-1-en-1-yl)-2,2-dimethylcyclopropane carboxylic acid (50% cis, 50% trans, w/w).

N.m.r. ($^1$H(ppm)CDCl$_3$): 1.18–1.51 (m,9H); 1.69–2.50 (m,2H) 4.27 (q,2H); 5.13 (2s,2H); 6.06, 6.79 (2d,1H).

Product H from 4-ethoxy-2,3,5,6-tetrafluorobenzyl alcohol and 3-(2,2-dichlorovinyl)-2,2-dimethylcyclopropane carboxylic acid (50% cis, 50% trans, w/w).

N.m.r. ($^1$H(ppm)CDCl$_3$): 1.15–1.52 (m,9H); 1.53–2.32 (m,2H) 4.29 (q,2H); 5.14 (2s,2H); 5.54, 6.17 (2d,1H)

Product J from 4-methyl-2,3,5,6-tetrafluorobenzyl alcohol and 3-(2,2-dichlorovinyl)-2,2-dimethylcyclopropane carboxylic acid (100% cis isomer).

Product K from 4-methyl-2,3,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.28 (s,6H); 1.92–2.44 (m,5H); 5.25 (s,2H); 6.92 (d,1H).

Infra red (liquid film): 3080, 1735, 1655, 1495, 1135 cm$^{-1}$.

Product L from 4-ethyl-2,3,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.14 (t,3H); 1.24 (s,6H); 1.92–2.28 (m,2H); 2.72 (q,2H); 5.14 (s,2H); 6.88 (d,1H).

Infra red (liquid film): 3080, 1735, 1655, 1495, 1135 cm$^{-1}$.

Product M from 4-methoxy-2,3,5,6-tetrafluorobenzyl alcohol and 3-(2,2-dichlorovinyl)-2,2-dimethylcyclopropane carboxylic acid (100% cis isomer).

N.m.r. ($^1$H(ppm)CDCl$_3$): 1.15–1.38 (m,6H); 1.55–2.33 (m,2H); 4.10 (d,3H), 5.19 (m,2H); 2.59, 6.22 (dd,1H).

Infra red (liquid film): 2950, 1730, 1650, 1500, 1160, 1140 cm$^{-1}$.

Product N from 4-n-butyl-2,3,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 0.98 (m,3H); 1.30 (s,6H); 1.20–1.76 (m,4H); 1.92–2.38 (m,2H); 2.65–2.91 (m,2H); 5.20 (t,2H); 6.90 (d,1H).

Infra red (liquid film): 2950, 1730, 1650, 1495, 1295, 1270 1200, 1140, 1050, 1000, 950 cm$^{-1}$.

Product O from 4-allyloxy-2,3,5,6-tetrafluorobenzyl alcohol and 3-(2-chloro-3,3,3-trifluoroprop-1-en-1-yl)-2,2-dimethylcyclopropane carboxylic acid (100% cis isomer.)

N.m.r. ($^1$H(ppm)CDCl$_3$): 1.26 (s,6H); 1.89–2.34 (m,2H); 4.72 (d,2H); 5.12–5.50 (m,4H); 5.80 (m,1H); 6.88 (d,1H).

Infra red (liquid film): 2950, 1730, 1650, 1495, 1295, 1270 1200, 1140, 1050, 1000, 950 cm$^{-1}$.

Product P from 4-methoxy-2,3,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.14 (s,6H); 1.85–2,25 (m,2H); 4.02 (d,3H); 5.10 (s,2H); 6.78 (d,1H).

Infra red (liquid film): 2950, 1730, 1650, 1500, 1300, 1275 1200, 1140, 1050, 950 cm$^{-1}$.

Product Q from 3-methyl-2,4,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.3 (s,6H); 2.0 (m,5H); 5.1 (m,2H); 6.8 (d,1H).

Infra red (liquid film): 1730, 1650, 1500, 1300, 1280, 1140 cm$^{-1}$.

Product R from 3-methyl-2,4,5,6-tetrafluorobenzyl alcohol and 3-(2,2-dichlorovinyl)-2,2-dimethylcyclopropane carboxylic acid (50% cis, 50% trans, w/w).

N.m.r. ($^1$H(ppm)CDCl$_3$): 1.2 (q,6H); 1.8 (m,2H); 2.2 (m,3H) 5.1 (m,2H); 5.5, 6.2 (dd,1H).

Infra red (liquid film): 1830, 1650, 1500, 1360, 1340, 1320 cm$^{-1}$.

Product S from 4-allyl-2,3,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.30 (s,6H); 1.90–2.32 (m,2H); 3.50 (m,2H); 4.95–5.30 (m,4H); 5.70–6.10 (m,1H); 6.90 (d,1H).

Infra red (liquid film): 2950, 1730, 1650, 1495, 1300, 1280, 1200, 1140, 950 cm$^{-1}$.

Product T from 4-n-propyl-2,3,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 0.94 (t,3H); 1.24 (s,6H); 1.60 (q,2H); 1.84–2.26 (m,2H); 2.66 (t,2H); 5.08 (s,2H); 6.72 (d,1H).

Infra red (liquid film): 3075, 1735, 1655, 1490, 1135 cm$^{-1}$.

Product U from 4-allyl-2,3,5,6-tetrafluorobenzyl alcohol and 3-(2,2-dichlorovinyl)-2,2-dimethylcyclopropane carboxylic acid (50% cis, 50% trans, w/w).

N.m.r. ($^1$H(ppm)CDCl$_3$): 1.20 (m,6H); 1.53–2.30 (m,2H); 3.41 (m,2H); 4.88–5.23 (m,4H); 5.59–6.00 (m,1H); 5.52, 6.14 (dd,1H).

Infra red (liquid film): 3960, 1730, 1640, 1495, 1280, 920, 880 cm$^{-1}$.

Product V from 4-(3-methylbut-2-en-1-yl)-2,3,5,6-tetrafluorobenzyl alcohol and 3-(2-chloro-3,3,3-trifluoromethylprop-1-en-1-yl)-2,2-dimethylcyclopropane caroxylic acid (100% cis isomer).

N.m.r. ($^1$H(ppm)CDCl$_3$): 1.27 (s,6H); 1.70 (d,6H); 1.83–2.29 (m,2H); 3.39 (m,2H); 4.90–5.25 (m,3H); 6.85 (d,1H).

Infra red (liquid film): 2950, 1730, 1650, 1495, 1300, 1280, 1200, 1180, 1140, 1050, 960, 860 cm$^{-1}$.

Product W from 4-(but-2-en-1-yl)-2,3,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.28 (s,6H); 1.58–1.82 (m,3H); 1.90–2.30 (m,2H); 3.35–3.60 (m,2H); 5.20–5.75 (m,4H); 6.92 (d,1H).

Infra red (liquid film): 2980, 1730, 1650, 1490, 1300, 1275, 1200, 1170, 1130, 950 cm$^{-1}$.

Product X from 4-allyl-2,6-difluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.3 (d,6H); 1.9 (d,1H); 2.15 (t,1H) 3.35 (d,2H); 5.1 (m,2H); 5.15 (s,2H) 5.8 (m,1H); 6.75 (d,2H); 6.95 (d,1H)

Infra red (liquid film): 1730, 1640, 1590, 1440 cm$^{-1}$.

Product Y from 4-allyl-3,5-difluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.31 (s,6H); 1.98–2.20 (m,2H); 3.43 (m,2H); 4.95–5.25 (m,4H); 5.78–6.20 (m,1H); 6.80–7.15 (m,3H).

Infra red (liquid film): 2960, 2920, 1730, 1640, 1590, 1440, 1410, 1360, 1300, 1270, 1200, 1170 1130, 1080, 960, 760 cm$^{-1}$.

Product Z from 4-benzyl-2,3,5,6-tetrafluorobenzyl alcohol and 3-(2-chloro-3,3,3-trifluoroprop-1-en-1-yl)-2,2-dimethylcyclopropane carboxylic acid (100% cis isomer).

N.m.r. ($^1$H(ppm)CDCl$_3$): 1.28 (s,6H); 1.88–2.30 (m,2H); 4.08 (s,2H); 5.20 (s,2H); 6.90 (d,1H); 7.28 (s,5H).

Infra red (liquid film): 3080, 1735, 1655, 1495, 1165 cm$^{-1}$.

I claim:

1. A compound of formula:

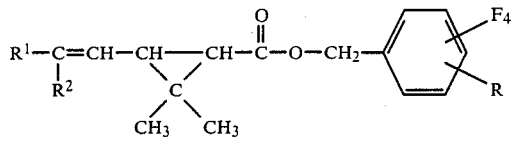

where $R^1$ and $R^2$ are both halo or both methyl and R is methyl, ethyl, allyl, methoxy, ethoxy or allyloxy.

2. A compound according to claim 1 selected from the group of
4-methyl-2,3,5,6-tetrafluorobenzyl (±)-cis-3-(2,2-dichlorovinyl)-2,2-dimethylcyclopropane carboxylate,
4-methoxy-2,3,5,6-tetrafluorobenzyl (±)-cis-3-(2,2-dibromovinyl)-2,2-dimethylcyclopropane carboxylate,
4-allyl-2,3,5,6-tetrafluorobenzyl (±)-cis/trans-3-(2,2-dichlorovinyl)-2,2-dimethylcyclopropane carboxylate.

3. An insecticidal composition comprising an insecticidally effective amount of a compound according to claim 1 in association with an agriculturally and horticulturally acceptable diluent.

4. A method of combating insect pests at a locus which comprises applying to the locus an insecticidally effective amount of a composition according to claim 3.

* * * * *